(12) United States Patent
Van Dyke

(10) Patent No.: US 9,763,654 B2
(45) Date of Patent: Sep. 19, 2017

(54) ADJUSTABLE ORTHOPAEDIC JOINT DISTRACTOR

(71) Applicant: Biomet Manufacturing, LLC, Warsaw, IN (US)

(72) Inventor: Scott Van Dyke, Columbia City, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 445 days.

(21) Appl. No.: 14/445,490

(22) Filed: Jul. 29, 2014

(65) Prior Publication Data
US 2016/0030028 A1    Feb. 4, 2016

(51) Int. Cl.
*A61B 17/60* (2006.01)
*A61B 17/02* (2006.01)
*A61B 17/64* (2006.01)

(52) U.S. Cl.
CPC ........ *A61B 17/025* (2013.01); *A61B 17/6425* (2013.01); *A61B 2017/0275* (2013.01)

(58) Field of Classification Search
CPC .......... A61B 17/025; A61B 2017/0275; A61B 17/0268
USPC ................................................. 606/86 R–89
See application file for complete search history.

(56) References Cited

U.S. PATENT DOCUMENTS

| | | | | |
|---|---|---|---|---|
| 5,597,379 A | * | 1/1997 | Haines ............... | A61B 17/1764 606/80 |
| 6,022,377 A | * | 2/2000 | Nuelle ................ | A61B 17/025 606/102 |
| 7,241,298 B2 | * | 7/2007 | Nemec ................ | A61B 17/15 606/86 R |
| 7,520,880 B2 | * | 4/2009 | Claypool ............. | A61B 17/155 606/246 |
| 2006/0149276 A1 | * | 7/2006 | Grimm ................ | A61B 17/157 606/88 |
| 2007/0208349 A1 | * | 9/2007 | Bastian ................ | A61B 17/154 606/87 |
| 2009/0043310 A1 | * | 2/2009 | Rasmussen .......... | A61B 17/025 606/88 |
| 2010/0004658 A1 | * | 1/2010 | Axelson, Jr. ......... | A61B 17/155 606/96 |
| 2013/0331843 A1 | * | 12/2013 | Rasmussen .......... | A61B 17/025 606/88 |
| 2015/0157467 A1 | * | 6/2015 | McGinley ............ | A61B 17/15 606/86 R |
| 2015/0305753 A1 | * | 10/2015 | McGinley .......... | A61B 17/1739 606/96 |

* cited by examiner

*Primary Examiner* — Matthew Lawson
(74) *Attorney, Agent, or Firm* — Schwegman Lundberg & Woessner, P.A.

(57) ABSTRACT

An orthopaedic joint distractor includes a stem post defining a pivoting axis, an actuator configured to cause translational movement of the stem post, a locking sleeve holding the actuator and the stem post, a distractor arc held by the locking sleeve orthogonally to the pivoting axis and having a surface, and a first locking member held by the locking sleeve that can be advanced away from and toward the surface. The first locking member prevents rotation of the distractor arc about the pivoting axis when it has advanced a sufficient distance toward the surface.

19 Claims, 7 Drawing Sheets

ADJUSTABLE ORTHOPAEDIC JOINT DISTRACTOR

BACKGROUND OF THE INVENTION

1. Field of the Invention

The present invention relates to orthopaedic devices, and, more particularly, to orthopaedic joint distractors.

2. Description of the Related Art

Joint distraction is a procedure performed in orthopaedics, either alone or as part of a larger procedure. Joint distraction involves separating the two bones that are connected by a joint away from each other. This separation can expose the joint so that arthroscopy can be performed or be held so that the joint is no longer bearing load from the two bones. When the distraction is performed to free the joint from bearing load, it is referred to as off-loading the joint.

When the joint is off-loaded, it is sometimes necessary to do so for extended periods of time. In the case of off-loading a hip joint, which is a joint between the acetabulum of the pelvis and the femur, the distraction can interfere with the patient's range of motion during their recovery. In particular, sitting from a standing position can be difficult.

What is needed in the art is a joint distractor that can cause less interference with a patient's range of motion.

SUMMARY OF THE INVENTION

The present invention provides a joint distractor with a distractor arc that can be adjusted to varying positions around a stem post of the joint distractor.

The invention in one form is directed to an orthopaedic joint distractor including a stem post defining a pivoting axis; an actuator configured to cause translational movement of the stem post; a locking sleeve holding the actuator and the stem post; a distractor arc held by the locking sleeve orthogonally to the pivoting axis and having a surface; and a first locking member held by the locking sleeve that can be advanced away from and toward said surface. The first locking member prevents rotation of the distractor arc about the pivoting axis when it has advanced a sufficient distance toward the surface.

The invention in another form is directed to method of distracting an orthopaedic joint, including the steps of positioning a distractor arc connected to a stem post by a locking sleeve in an unlocked state adjacent to a proximal bone, with the stem post defining a pivoting axis and the distractor arc being rotatably adjustable relative to the pivoting axis when unlocked. The distractor arc, stem post and locking sleeve are fixated to the proximal bone and the stem post is connected to a distal bone using a fixator. The distractor arc is locked so that the distractor arc is no longer rotatably adjustable relative to the pivoting axis.

The invention in yet another form is directed to an orthopaedic joint distractor kit, that includes a package. The package contains a stem post; an actuator configured to cause translation of the stem post; a locking sleeve including a stem post holder that is configured to hold the stem post and the actuator, an arc holder that is formed in or connected to the locking sleeve orthogonally to the stem post holder and a first locking holder; a distractor arc sized to be held by the arc holder and rotate about the stem post holder; and a first locking member sized to be held by the first locking holder. The first locking member is configured to prevent rotation of the distractor arc about the stem post holder when the first locking member is held in a locking position by the first locking holder.

An advantage of the present invention is that the radial position of the arc distractor relative to the stem post can be adjusted. This adjustability provides more options for the surgeon and can increase the patient's range of motion when the joint distractor is off-loading the joint.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
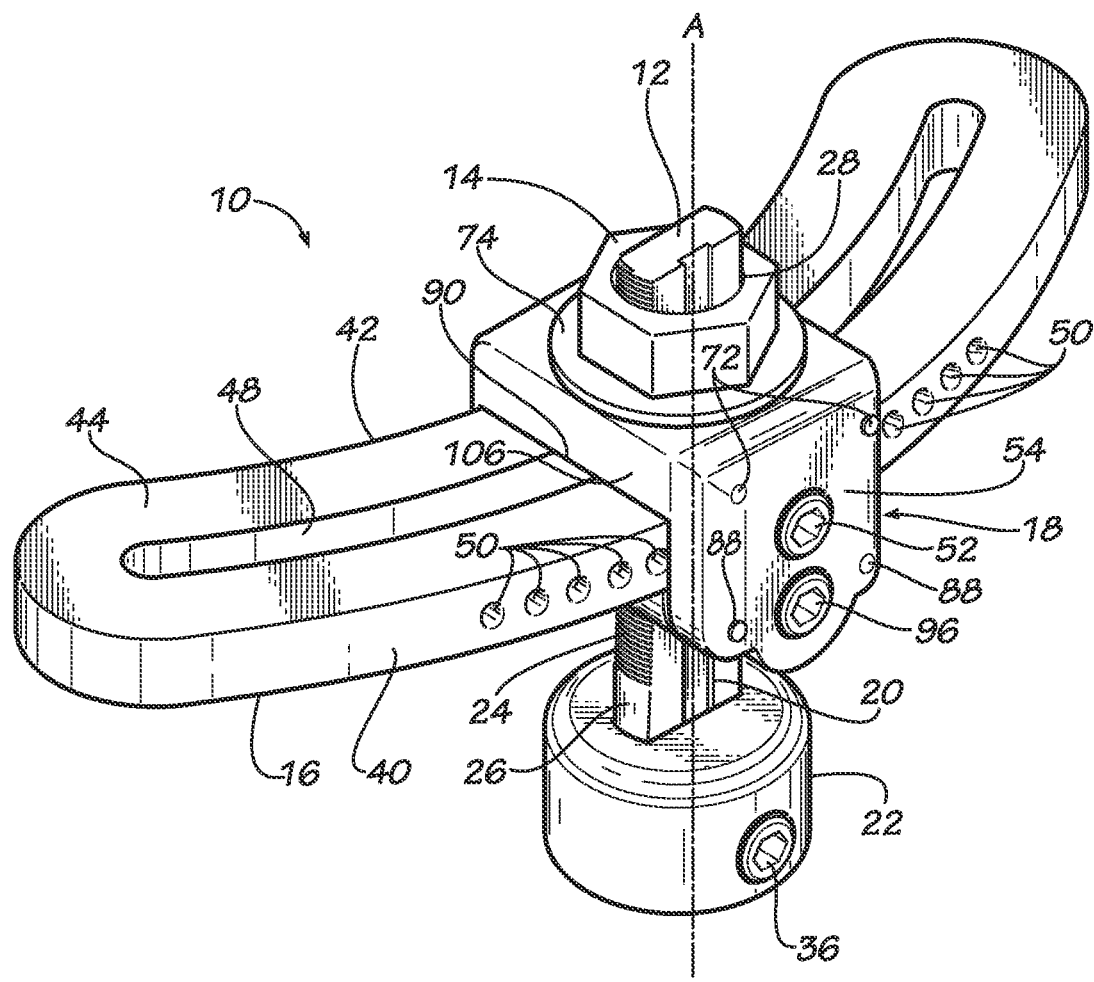
FIG. 1 is a perspective view of an orthopaedic joint distractor of the present invention.

Referring now to the drawings, and more particularly to FIG. 1, there is shown an orthopaedic joint distractor 10 which generally includes a stem post 12, an actuator 14 that can translate the stem post 12, a distractor arc 16, and a locking sleeve 18 holding the stem post 12, actuator 14 and distractor arc 16. The locking sleeve 18 holds the stem post 12, actuator 14 and distractor arc 16 in a manner such that they can either be in an "unlocked" state or in a "locked" state. In the unlocked state, the distractor arc 16 can be rotated as it is held by the locking sleeve 18, allowing for the orthopaedic joint distractor 10 to be adjustable. In the locked state, the distractor arc 16 is firmly held by the locking sleeve 18 and not freely adjustable. The ways in which the locking sleeve 18 can hold the stem post 12, actuator 14 and distractor arc 16 in either the unlocked or locked state will be described further below.

Figure 3:
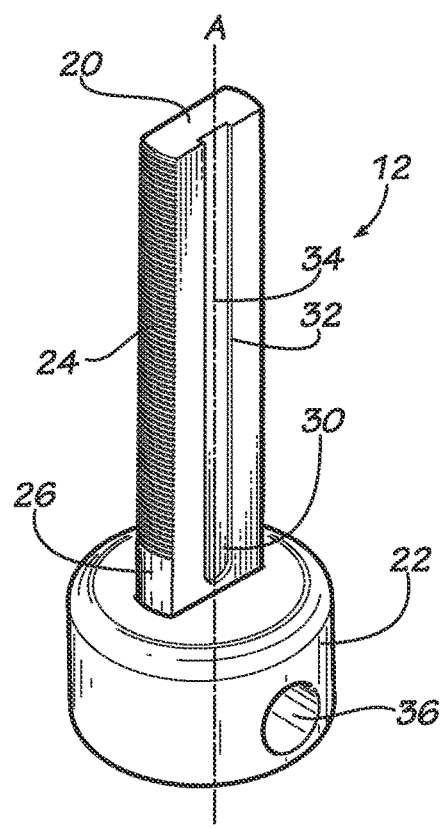
FIG. 3 is a perspective view of the stem post shown in FIG. 1.

As can be seen in FIGS. 1 and 3, the stem post 12 includes an elongated portion 20 connected to a base 22 and defines a pivoting axis A along its length. The elongated portion 20 is shown as having a substantially rectangular cross-section and the base 22 is shown as having a circular cross-section, but other shapes are contemplated as being used for the elongated portion 20 and base 22. The elongated portion 20 can have notches 24 formed on side surfaces 26 that will interact with the actuator 14, shown in FIG. 1 as a nut, to allow for translational movement of the stem post 12 through an opening 28 formed in the nut 12. Features (not shown) formed on an interior surface of the opening 28 are keyed to the notches 24 so that rotation of the nut 12 will cause the stem post 12 to move along the pivoting axis A. The stem post 12 can also have a face 30 with a slot 32 formed thereon that provides a flat surface 34, for reasons that will be described below. The base 22 can include a fixator connector 36 that allows for the stem post 12 to be connected to a fixator 38 (shown in FIGS. 6-8). When the orthopaedic joint distractor 10 is used, the translational movement of the stem post 12 will cause the separation of the bones surrounding the joint. As such, the stem post 12 and actuator 14 can be configured as any shape and from any material that allows for a separation of the bones surrounding the joint to be effectuated. Particularly, the actuator 14 need not be a nut, as shown, but could be any type of mechanism that can cause the stem post 12 to move along the pivoting axis A when held by the locking sleeve 18.

Figure 2:
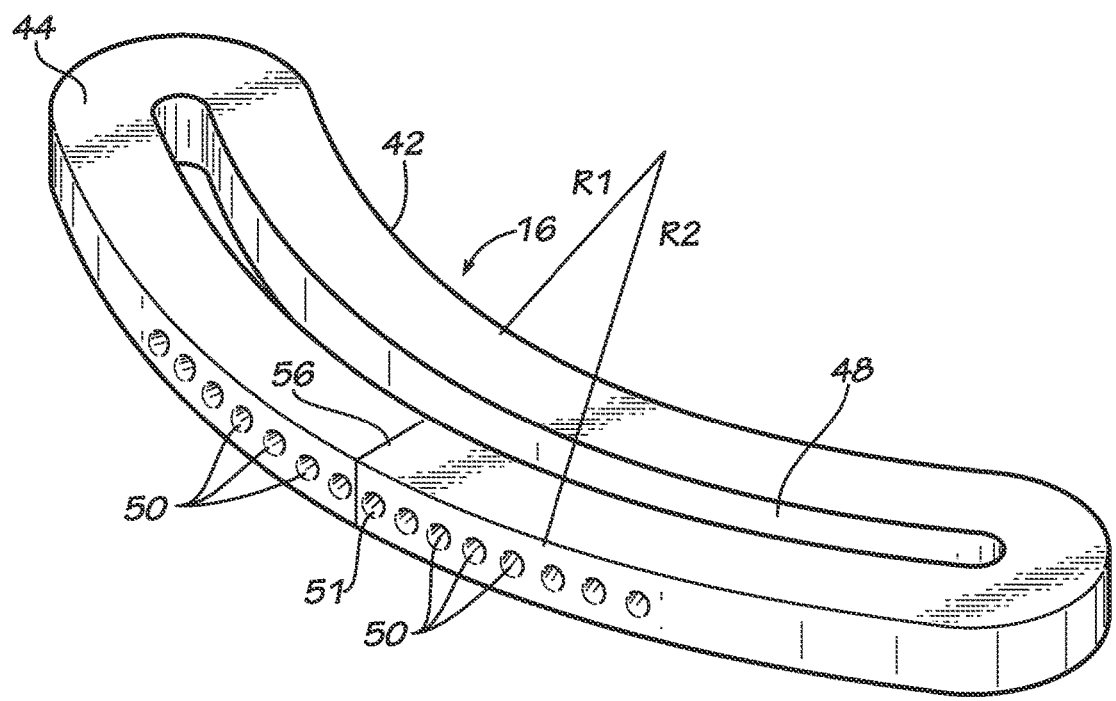
FIG. 2 is a perspective view of the distractor arc shown in FIG. 1.

The distractor arc 16, as shown in FIGS. 1 and 2, has a curvature defined by arc radii R1 and R2. Arc radii R1 and R2 can be adjusted as desired to give the distractor arc 16 a desired curvature for use in an orthopaedic joint distraction procedure. The distractor arc 16 has a circumferential surface 40, an inner arc surface 42, a top surface 44 and a bottom surface 46. The distractor arc 16 can have an elongated opening 48 formed through the top and bottom surfaces 44, 46 between the circumferential surface 40 and the inner arc surface 42. The elongated opening 48 can be sized and shaped so that the elongated portion 20 of the stem post 12 can be held within the elongated opening 48, allowing the stem post 12 to be moved along the elongated opening 48, the distractor arc 16 to be rotated about the pivoting axis A, or both.

The distractor arc 16 can include multiple locking features 50 on one or more of the arc's 16 surfaces 40, 42, 44, 46. The locking features 50, shown as openings in FIGS. 1 and 2, can interface with a locking member 52, shown as a set screw in FIG. 1, so that the locking member 52 reversibly interferes with the distractor arc's 16 ability to freely rotate about the stem post 12, which will be described in detail below. The locking features 50 and locking member 52 can take on a variety of shapes and sizes, so long as they are complementary to one another and can prevent free rotation of the distractor arc 16 about the pivoting axis A when the locking feature(s) 50 and member 52 are interfaced. In this respect, the locking features 50 and locking member 52 can be configured as many different complementary shapes. Similarly, the locking features 50 can be placed on any of the surfaces 40, 42, 44, 46 of the distractor arc 16, with the locking member's 52 position on the locking sleeve 18 being adjusted so that it can interface with the locking features 50. As shown in FIGS. 1 and 2, the locking features 50 are placed along the circumferential surface 40 of the distractor arc 16 and the locking member 52 is held in a front face 54 of the locking sleeve 18. The locking features 50 can also have an adjustable spacing between one another, which allows for different radial positions of the distractor arc 16 to be chosen relative to the pivoting axis A when a locking feature 50 is interfaced with the locking member 52. The spacing can either vary between the locking features 50, or can be uniform between the locking features 50, depending on the intended application of the orthopaedic joint distractor 10.

As shown in FIG. 2, the distractor arc 16 can have one or more visual indicators 56 placed near a locking feature 50. The visual indicators 56 can be a variety of things that can be seen by a user, including markings, notches, protrusions, lettering, etc. When the distractor arc 16 includes multiple locking features 50, the visual indicator(s) 56 can indicate a variety of radial positions of the distractor arc 16, relative to the pivoting axis A, that correspond to different allowable ranges of motion, correct positioning for a particular type of surgery, or both. The visual indicator(s) 56 could also be paired together to assist the user, e.g., a marking line accompanied by numbering that indicates the angle formed between the marking line's associated locking feature 50 and a central locking feature 51.

Figure 4:
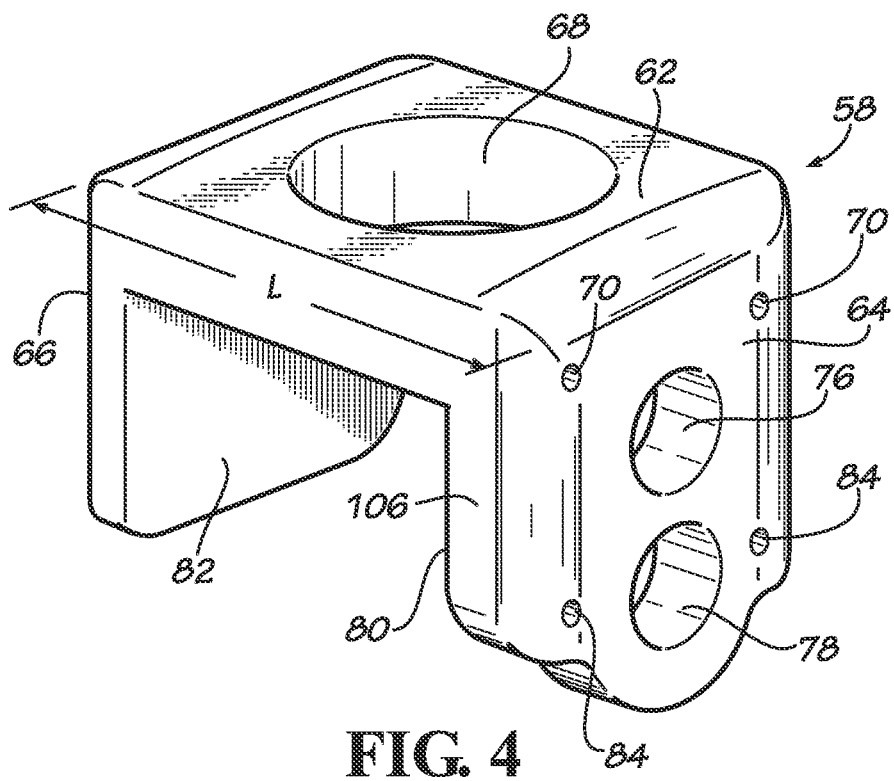
FIG. 4 is a perspective view of the top portion of the locking sleeve shown in FIG. 1.
Figure 5:
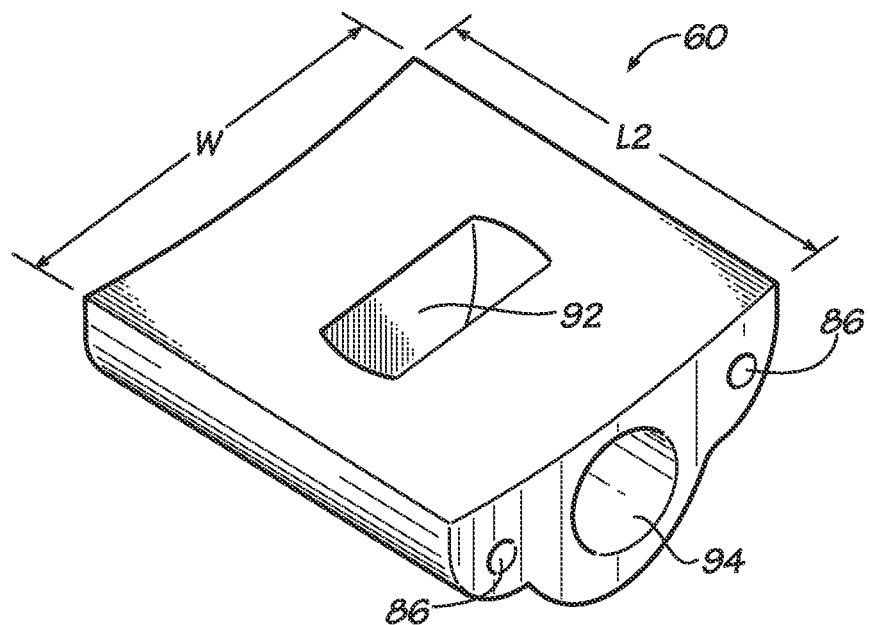
FIG. 5 is a perspective view of the bottom portion of the locking sleeve shown in FIG. 1.

The locking sleeve 18, as shown in FIGS. 1, 4 and 5, holds the stem post 12, actuator 14 and distractor arc 16 together during use of the orthopaedic joint distractor 10. The locking sleeve 18 can either be a multi-piece design, as shown, or could also be a single piece if desired. When configured as a multi-piece element, the locking sleeve 16 can have a top portion 58, shown in detail in FIG. 4, and a bottom portion 60, shown in detail in FIG. 5.

Referring now to FIG. 4, the top portion 58 can have a top surface 62 and a front surface 64 and rear surface 66 that both extend perpendicularly to the top surface 62. The top portion 58 can be open on the bottom, which can be connected to the bottom portion 60 to close the locking sleeve 18. The top surface 62 can have a stem post opening 68 formed through that is sized to allow the stem post 12 to pass through and hold the actuator 14. The stem post opening 68, as shown, has a circular shape to accommodate the actuator 14, which is configured as a nut, but could have other shapes to accommodate the stem post 12, the actuator 14, or both. A pair of pin openings 70 can pass through the front surface 64 and intersect one or more points on the circumference of the stem post opening 68. Pins 72 (shown in FIG. 1) can be placed through the pin openings 70 to fit inside channels (not shown) formed along the circumference of a circular base 74 of the actuator 14 inside the stem post opening 68, holding the actuator 14 to the locking sleeve 18 while still allowing the actuator 14 to rotate. The front surface 64 can also have a first locking opening 76 that can hold locking member 52 and a second locking opening 78 that can hold second locking member 80. The length L of the top surface 62 can be chosen to be slightly more than a distance between the circumferential surface 40 and inner arc surface 42 of the distractor arc 16, so that the distractor arc 16 can be held between the front surface 64 and rear surface 66 when the top portion 58 is connected to the bottom portion 60. The front surface 64 can have a curved inner wall 80 and the rear surface 66 can also have a curved inner wall 82. The curved inner walls 80, 82 can be shaped so that the distractor arc 16 can rotate smoothly when held by the locking sleeve 18 between the front surface 64 and rear surface 66. The front surface 64 can also have a pair of sleeve pin openings 84 that can correspond to sleeve pin openings 86 (shown in FIG. 5) formed on the bottom portion 60. Sleeve pins 88 be pass through the sleeve pin openings 84, 86 to hold the top portion 58 to the bottom portion 60, keeping the locking sleeve 18 in an assembled state.

Referring now to FIG. 5, the bottom portion 60 can have a substantially semi-cylindrical shape with a length L2 and width W that allow the bottom portion 60 to fit between the front surface 64 and rear surface 66 of the top portion 58 in a way that creates an enclosed arc opening 90 in the locking sleeve 18. When the arc distractor 16 is held in the arc opening 90, its movement is limited to rotation about the pivoting axis A by the top surface 62, bottom portion 60, front surface 64 and rear surface 66. The bottom portion 60 can also have a second stem post opening 92 formed through that will align with the stem post opening 68 when the locking sleeve 18 is assembled, allowing the stem post 12 to pass through both stem post openings 68, 92 when translated by the actuator 14. Similarly, the bottom portion 60 can also have a third locking opening 94 that continues into the second stem post opening 92 and aligns with the second locking opening 78 when the locking sleeve 18 is assembled. The third locking opening 94 is sized similarly to the second locking opening 78 to allow a second locking member 96 to pass through both the second and third locking openings 78, 94. When the orthopaedic joint distractor 10 is assembled, as shown, the stem post 12 will be held within the stem post opening 68 and second stem post opening 92, with the slot 32 facing the second locking opening 78 and third locking opening 94. When the stem post 12 is at a desired position, the second locking member 96 can be advanced through the stem post openings 68, 92 toward the flat surface 34 of the slot 32 and pressed into the flat surface 34. Pressing the second locking member 96 into the flat surface 34 creates friction between the second locking member 96 and the stem post 12. If the second locking member 96 is pressed with enough force into the flat surface 34, enough friction is created to prevent translational movement of the stem post 12.

While the locking sleeve 18 is shown as holding the stem post 12 in stem post openings 68 and 92; the actuator in stem post opening 68; and the arc distractor 16 in arc opening 90, it is also contemplated that the locking sleeve 18 could hold the stem post 12, actuator 14 and arc distractor 16 together in other ways, such as various types of connections to surfaces of the locking sleeve 18. In such a configuration, the stem post 12, actuator 14 and distractor arc 16 would each be held by a holder that is held by or part of the locking sleeve 18. In this respect, the openings 68, 92, 90 that are shown as holding the stem post 12, actuator 14 and distractor arc 16 in FIGS. 1-8 could also be considered holders. To allow the arc distractor 16 to rotate about the pivoting axis A defined by the stem post 12, the locking sleeve 18 holds the arc distractor 16 generally orthogonally to the pivoting axis A. As used here, "generally orthogonally" refers to a mostly perpendicular orientation of the distractor arc 16 relative to the pivoting axis A, with a tolerance of about 5 degrees. In this respect, the distractor arc 16 can be held within or to the locking sleeve 18 in a variety of ways without straying from the scope of the present invention.

Figure 6:
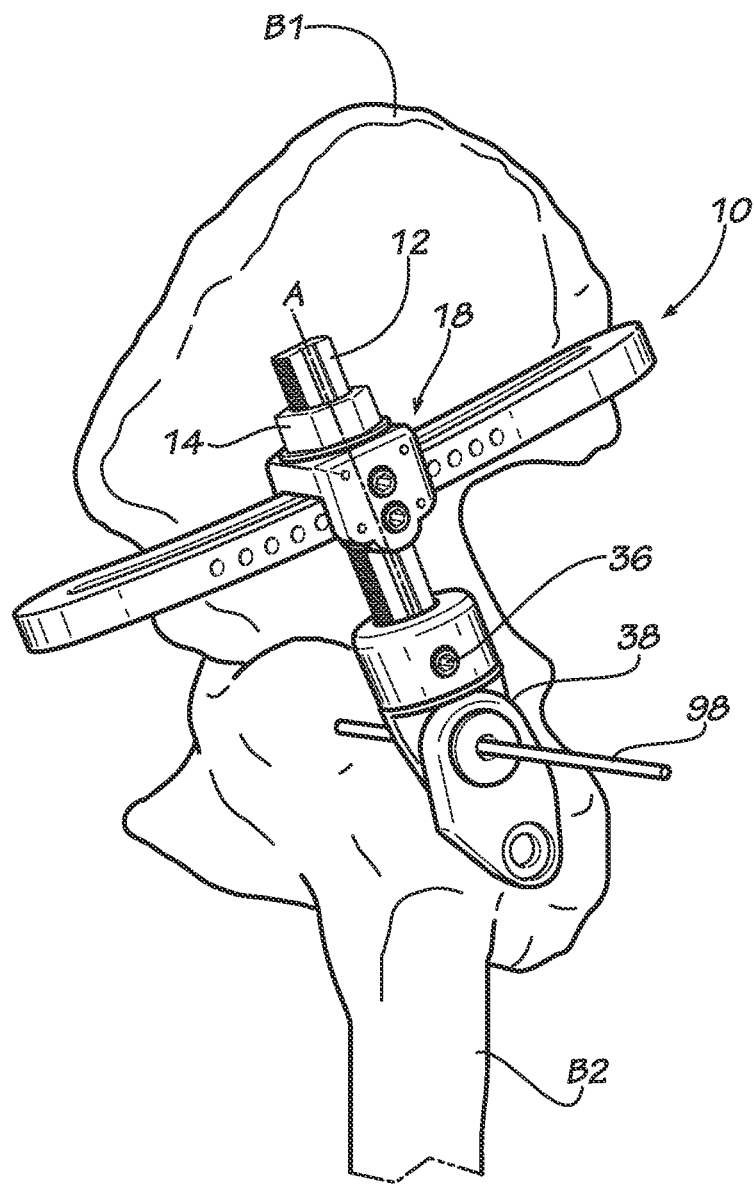
FIG. 6 is a perspective view of the orthopaedic joint distractor shown in FIG. 1 being used in an orthopaedic procedure.
Figure 7:
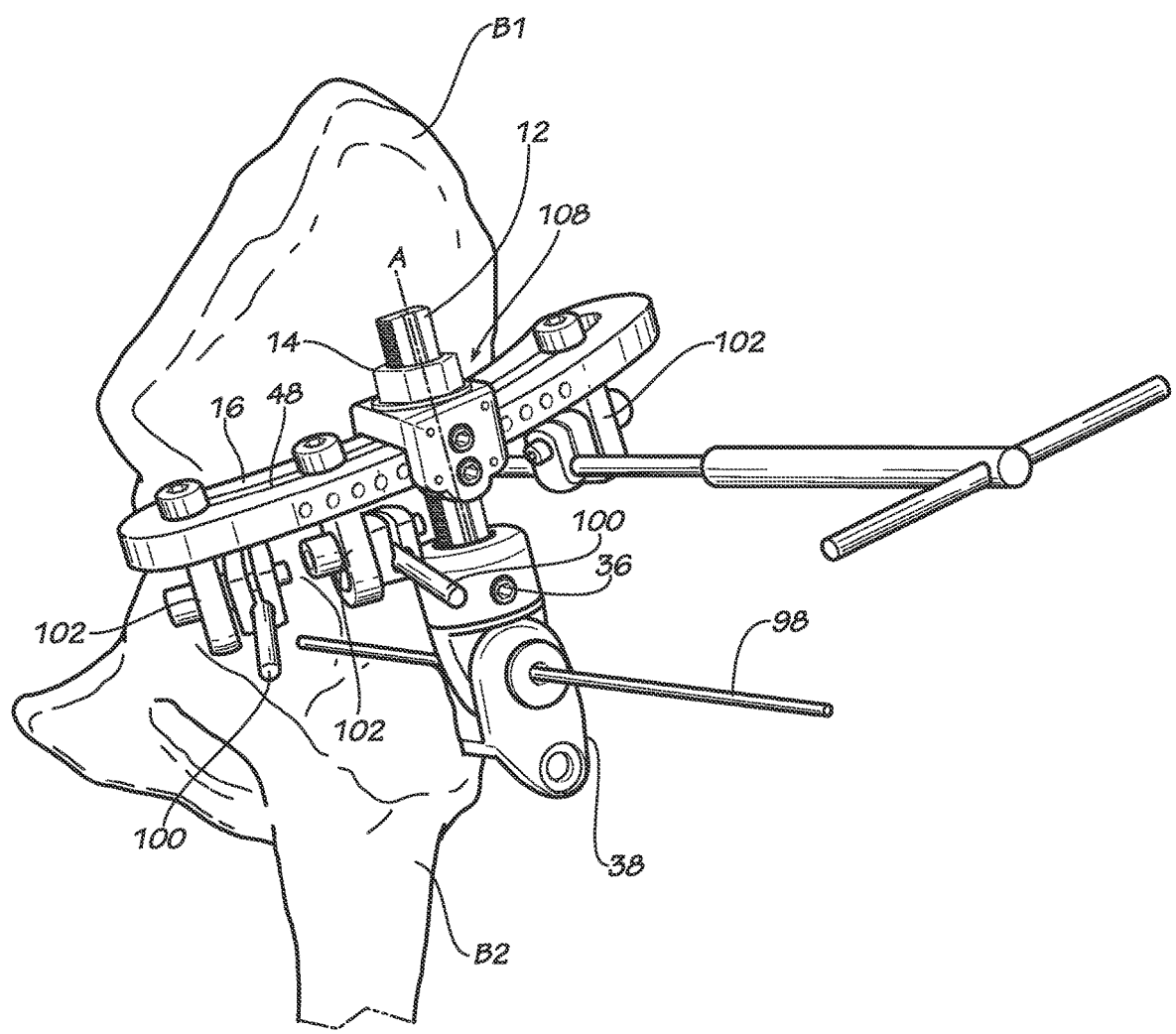
FIG. 7 is a perspective view of a further step of the orthopaedic procedure shown in FIG. 6.
Figure 8:
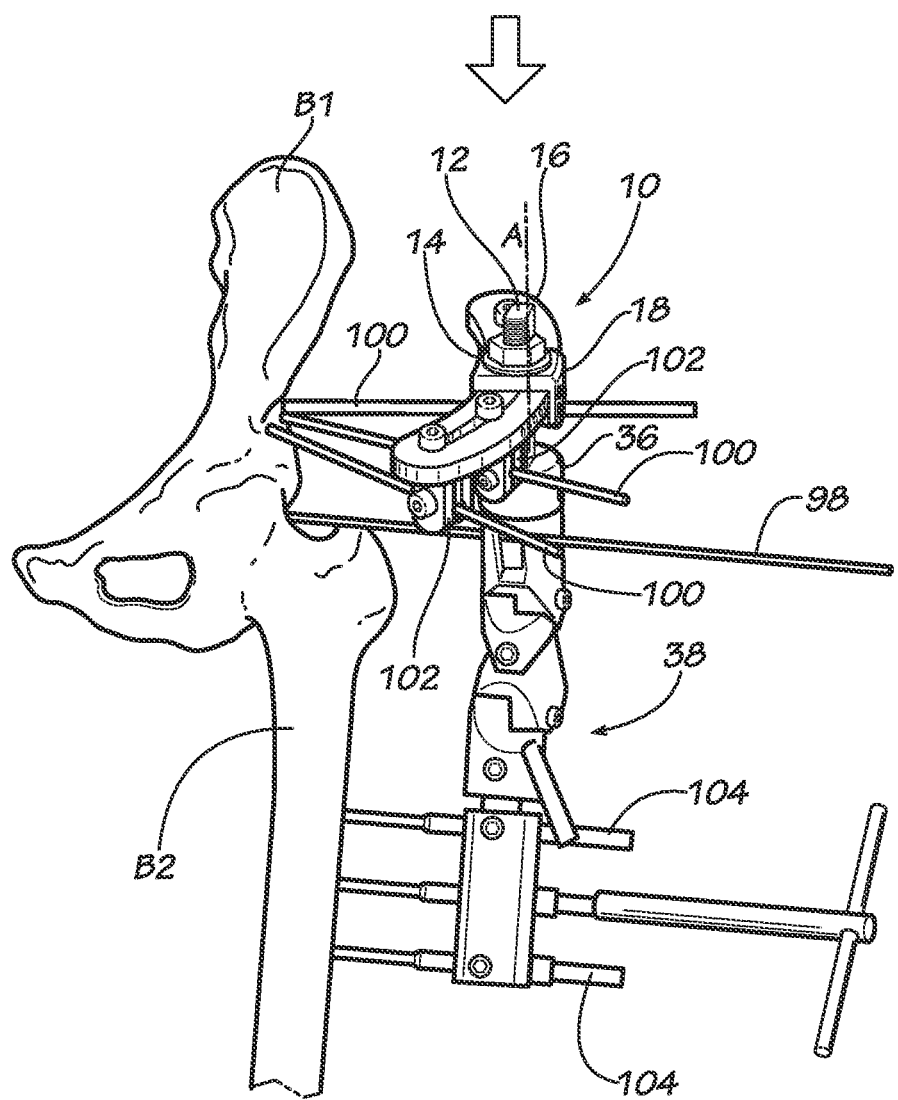
FIG. 8 is a perspective view of a further step of the orthopaedic procedure shown in FIG. 7.

To use the orthopaedic joint distractor 10 of the present invention, the joint distractor 10 is assembled so that the locking sleeve 18 is holding the stem post 12, actuator 14 and distractor arc 16 together. The joint distractor 10 can be assembled in an unlocked state, i.e., the distractor arc 16 can be rotated about the pivoting axis A defined by the stem post 12. In the unlocked state, the locking member 52 can be placed in the first locking opening 76 of the locking sleeve 18, but it is not advanced toward the distractor arc 16 such that it is contacting the distractor arc 16 and/or interacting with a locking feature 50 of the distractor arc 16. As shown in FIG. 6, the joint distractor 10 is positioned so that it is aligned with a proximal bone B1, such as a pelvis, and the fixator connector 36 is connected to a portion of the fixator 38. A guide wire 98, such as a k-wire, is placed through the fixator 38 to a distal bone B2, such as a femur, to maintain the orientation of the joint distractor 10 and fixator 38 and ensure that the pivoting axis A is properly aligned relative to the proximal bone B1. Guide holes can be drilled into the proximal bone B1 so that bone screws 100 can be inserted into the proximal bone B1 in a desired position, as shown in FIG. 7. The bone screws 100 can be any type of bone screw suitable for orthopaedic surgeries. To fixate the joint distractor 10 to the proximal bone B1, bone screws 100 can be connected to the distractor arc 16, in an exemplary fashion, by holding screw arms 102 which are attached to the bone screws 100 in the elongated opening 48 of the distractor arc 16. The bone screws 100 could also be attached to the distractor arc 16 directly, if desired, or the joint distractor 10 could be fixated to the proximal bone in other ways. The fixator 38 can also be fixated to the distal bone B2 using bone screws 104, as shown in FIG. 8.

Since the fixator 38 is connected to the fixator connector 36 of the stem post 12, the stem post 12 and attached locking sleeve 18 will be locked in place relative to the distal bone B2 if connected to the fixator 38 when it is fixated to the distal bone B2. If the joint distractor 10 is unlocked, the distractor arc 16 can rotate about the pivoting axis A when the stem post 12 is locked in place relative to the distal bone B2. This allows the radial positioning of the distractor arc 16 relative to the pivoting axis A to be adjusted, as desired. Once the distractor arc 16 is in a correct positioning, which can be indicated by one or more visual indicators 56 aligning with a side surface 106 of the locking sleeve 18, the joint distractor 10 can be locked so that the distractor arc 16 is no longer freely rotatable about the pivoting axis A. To lock the joint distractor 10, the locking member 52 is advanced toward a surface 40, 42, 44, 46 of the distractor arc 16 a sufficient distance so that the locking member 52 interfaces with one or more locking features 50 formed on the targeted surface 40, 42, 44, 46 and locks the distractor arc 16 in place or the locking member 52 is pressed into the targeted surface 40, 42, 44, 46 with sufficient force to create friction that locks the distractor arc 16 in place. For example, the joint distractor 10 shown in FIGS. 1 and 6-8 would be locked when the locking member 52, shown as a set screw, is advanced through the first locking opening 76 in the locking sleeve 18 into a locking feature 50, shown as an opening, on the circumferential surface 40 of the distractor arc 16. Once the set screw 52 is advanced into the opening 50, rotation of the distractor arc 16 about the pivoting axis A is prevented and the joint distractor 10 is in the locked state. Therefore, the locking feature 50 is in a locking position when it interferes with rotation of the distractor arc 16 about the pivoting axis A. As can be seen, the joint distractor 10 can be readily locked and unlocked to adjust the radial positioning of the distractor arc 16 relative to the pivoting axis A by adjusting the distance of the locking member 52 from the targeted surfaces 40, 42, 44, 46 of the distractor arc 16 and/or the interface feature(s) 50 on the targeted surface 40, 42, 44, 46. The joint distractor 10 can be unlocked from the locked state, as shown in FIG. 1, by advancing the set screw 52 out of an opening 50 on the circumferential surface 40 so that it no longer interferes with rotation of the distractor arc 16 about the pivoting axis A. The distractor arc's 16 radial positioning can then be adjusted before re-locking the joint distractor 10.

When the joint distractor 10 is locked, the locking sleeve 18 holds the stem post 12, actuator 14 and distractor arc 16 firmly together. The actuator 14 can be activated in the locked state to translate the stem post 12 in a direction toward the distal bone, indicated by an arrow in FIG. 8. The stem post 12 is connected to the fixator 38, which is fixated to the distal bone B2, so this translation causes separation of the distal bone B2 away from the proximal bone B1 and distraction of the joint between the proximal and distal bones B1 and B2. Once the desired separation is achieved, the stem post 12 can be locked by advancing the second locking member 96 through the second locking opening 78 and third locking opening 94 toward the flat surface 34 of the side post 12. The second locking member 96 is advanced toward the flat surface 34 until it presses into the flat surface 34 with a sufficient force to prevent the stem post 12 from translating further, locking the stem post 12 in place. Further surgical procedures can then be performed or the joint can remain off-loaded. If the joint is to remain off-loaded, the range of motion of the joint may be limited by the radial positioning of the distractor arc 16 relative to the pivoting axis A. If that is the case, a user can unlock the joint distractor 10, in the manner previously described, and adjust the radial positioning of the distractor arc 16 relative to the pivoting axis A. The adjusted radial positioning of the distractor arc 16 can allow for different ranges of motion, such as sitting from a standing position, to be achieved that a non-adjustable joint distractor may not allow.

Figure 9:
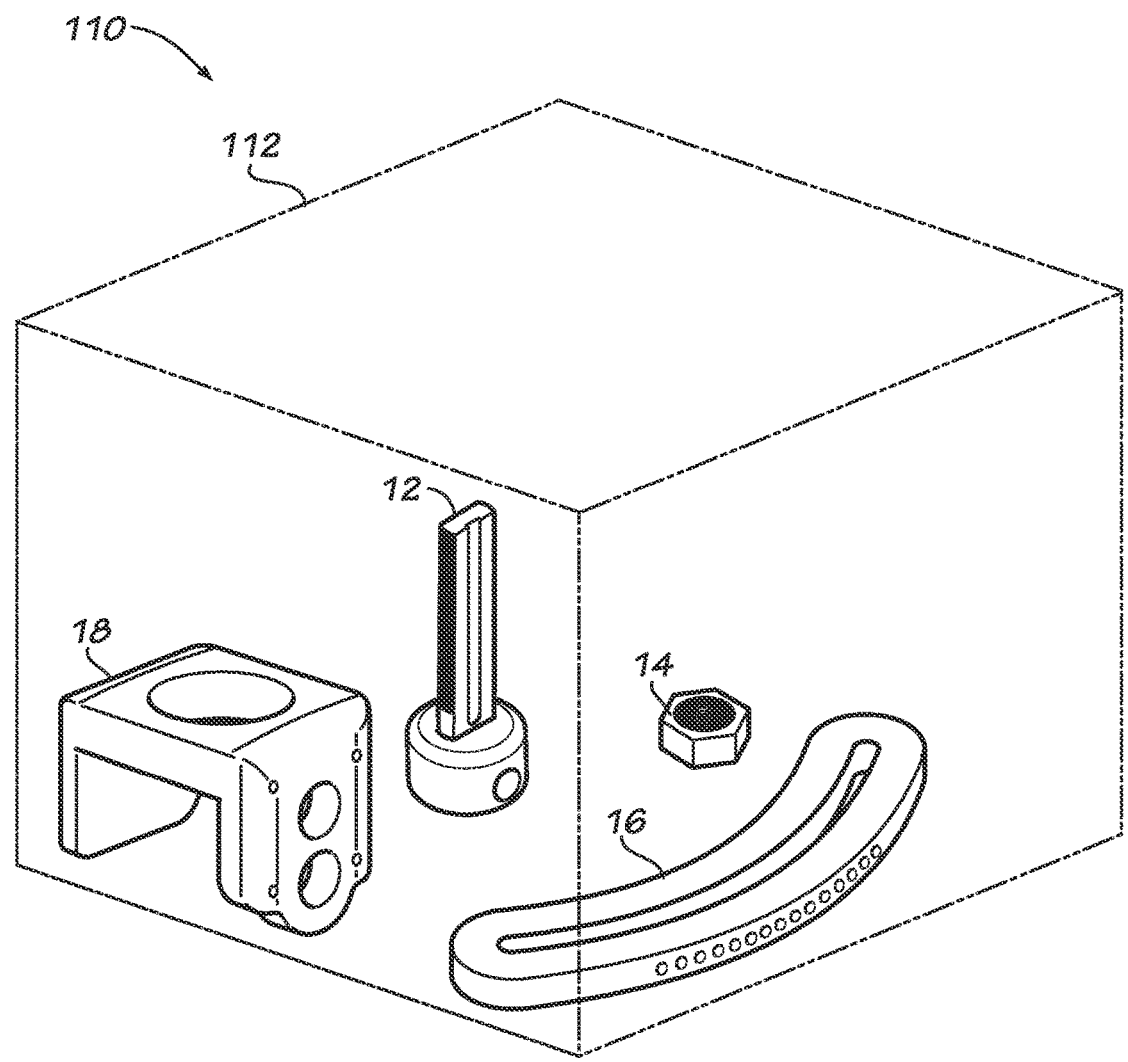
FIG. 9 is a perspective view of an orthopaedic joint distractor kit of the present invention.

Although the orthopaedic joint distractor 10 of the present invention has been described in a partially or mostly assembled state, it is contemplated that an orthopaedic joint distractor kit 110 can be produced that contains a stem post 12, an actuator 14, a distractor arc 16 and a locking sleeve 18 to assemble an orthopaedic joint distractor 10 of the present invention, as shown in FIG. 9. The orthopaedic joint distractor kit 110 can include a package 112 that will hold the components 12, 14, 16, 18 of the orthopaedic joint distractor 10. Any suitable arrangement and method of packaging the components 12, 14, 16, 18 in the package 112 for later use during an orthopaedic procedure are contemplated by the present invention. The package 112 can be either sterile or non-sterile and can also include other devices for performing a surgical procedure such as a drill guide, orthopaedic bone screws, etc. The components 12, 14, 16, 18 can either be completely separated in the package 112 or partially assembled together. Optionally, each component 12, 14, 16, 18 can be packaged separately within the package 112.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic joint distractor, comprising:
a stem post defining a pivoting axis;
an actuator configured to cause translational movement of said stem post;
a locking sleeve holding said actuator and said stem post;
a distractor arc held by said locking sleeve orthogonally to said pivoting axis and having a surface; and
a first locking member held by said locking sleeve that is configured to be advanced away from and toward said surface, said first locking member preventing rotation of said distractor arc about said pivoting axis when engaged with said surface;
wherein said distractor arc has a plurality of visual indicators on said surface that correspond to a plurality of discrete locking positions of the distractor arc relative to the locking sleeve.

2. The orthopaedic joint distractor according to claim 1, wherein said surface is a circumferential surface.

3. The orthopaedic joint distractor according to claim 2, wherein said distractor arc has an inner arc surface opposed to said circumferential surface.

4. The orthopaedic joint distractor according to claim 3, wherein said distractor arc has an elongated opening formed between said circumferential surface and said inner arc surface.

5. The orthopaedic joint distractor according to claim 4, wherein said stem post is held within said elongated opening.

6. The orthopaedic joint distractor according to claim 2, wherein portions of said circumferential surface and said inner arc surface are simultaneously held within said opening.

7. The orthopaedic joint distractor according to claim 1, wherein said surface includes a plurality of locking features formed thereon, at least one of said locking features being configured to interface with said first locking member, wherein each of the plurality of discrete locking positions corresponds to one of the plurality of locking features aligning with said first locking member.

8. The orthopaedic joint distractor according to claim 7, wherein said plurality of locking features are equally spaced from one another along said surface.

9. The orthopaedic joint distractor according to claim 1, wherein said locking sleeve holds a second locking member configured to prevent translational movement of said stem post.

10. The orthopaedic joint distractor according to claim 9, wherein said stem post includes a slot formed thereon, said slot having a flat surface and being sized to allow said second locking member to contact said flat surface.

11. An orthopaedic joint distractor system, comprising:
a package, said package containing:
a stem post including a slot formed thereon, said slot having a flat surface;
an actuator configured to cause translation of said stem post;
a locking sleeve including:
a stem post holder that is configured to hold said stem post and said actuator;
an arc holder that is one of formed in and connected to said locking sleeve orthogonally to said stem post holder and a first locking holder; and
a second locking holder;
a distractor arc sized to be held by said arc holder and rotate about said stem post holder;
a first locking member sized to be held by said first locking holder, said first locking member being configured to prevent rotation of said distractor arc about said stem post holder when said first locking member is held in a locking position by said first locking holder; and
a second locking member held by said second locking holder and configured to prevent translational movement of said stem post, said second locking member configured to engage said flat surface of said slot of the stem post.

12. The system according to claim 11, wherein said distractor arc includes a plurality of locking features sized to interface with said first locking member.

13. The system according to claim 11, wherein said distractor arc includes at least one visual indicator adjacent to at least one of said locking features.

14. The system according to claim 11, wherein said distractor arc includes an elongated opening sized to hold said stem post.

15. An orthopaedic joint distractor, comprising:
a stem post defining a pivoting axis;
an actuator configured to cause translational movement of said stem post;
a locking sleeve holding said actuator and said stem post;
a distractor arc held by said locking sleeve orthogonally to said pivoting axis and having a surface, said distractor arc having an elongated opening, wherein said stem post is held within said elongated opening; and
a first locking member held by said locking sleeve that is configured to be advanced away from and toward said surface, said first locking member preventing rotation of said distractor arc about said pivoting axis when engaged with said surface.

16. The orthopaedic joint distractor according to claim 15, wherein said surface is a circumferential surface and said distractor arc has an inner arc surface opposed to said circumferential surface.

17. The orthopaedic joint distractor according to claim 16, wherein said elongated opening is formed between said circumferential surface and said inner arc surface.

18. The orthopaedic joint distractor according to claim 15, wherein said distractor arc has at least one visual indicator on said surface that corresponds to a correct locking position.

19. The orthopaedic joint distractor according to claim 15, wherein:
said locking sleeve holds a second locking member configured to prevent translational movement of said stem post; and
said stem post includes a flat surface for contacting said second locking member.

* * * * *